US007619134B2

(12) United States Patent
Broglie et al.

(10) Patent No.: US 7,619,134 B2
(45) Date of Patent: Nov. 17, 2009

(54) STARCHES PRODUCED BY THE EXPRESSION OF HETEROLOGOUS GRANULE BOUND STARCH SYNTHASE GENES

(75) Inventors: Karen E. Broglie, Landenberg, PA (US); Jonathan Lightner, Mulino, OR (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 289 days.

(21) Appl. No.: 11/542,580

(22) Filed: Oct. 3, 2006

(65) Prior Publication Data

US 2007/0022500 A1    Jan. 25, 2007

Related U.S. Application Data

(63) Continuation of application No. 10/362,492, filed as application No. PCT/US00/23494 on Aug. 28, 2000, now abandoned.

(51) Int. Cl.
| | |
|---|---|
| C12N 15/82 | (2006.01) |
| C12N 15/63 | (2006.01) |
| C12N 15/52 | (2006.01) |
| A01H 5/10 | (2006.01) |
| A01H 5/00 | (2006.01) |
| C08B 30/00 | (2006.01) |

(52) U.S. Cl. ............... 800/284; 800/278; 800/285; 800/286; 800/320.1; 435/320.1; 435/468; 536/23.1; 536/23.6; 127/32

(58) Field of Classification Search .............. None
See application file for complete search history.

(56) References Cited

U.S. PATENT DOCUMENTS

| | | | |
|---|---|---|---|
| 3,830,697 A | | 8/1974 | Yoshida et al. |
| 5,300,145 A | * | 4/1994 | Fergason et al. ............ 536/102 |
| 5,830,724 A | | 11/1998 | Burrell et al. |
| 6,307,125 B1 | * | 10/2001 | Block et al. ................. 800/284 |
| 6,570,008 B1 | * | 5/2003 | Broglie et al. ............... 536/102 |
| 6,815,581 B2 | * | 11/2004 | Kossmann et al. .......... 800/284 |

FOREIGN PATENT DOCUMENTS

| | | |
|---|---|---|
| EP | 0 521 621 A2 | 7/1993 |
| EP | 0 584 809 A2 | 3/1994 |
| EP | 0 945 487 A2 | 3/1999 |
| WO | WO 95/35026 A1 | 12/1995 |
| WO | WO 97/16554 A1 | 5/1997 |
| WO | WO 97/26362 A1 | 7/1997 |
| WO | WO 97/45545 A1 | 12/1997 |
| WO | WO9745545 * | 12/1997 |
| WO | WO 98/44780 A1 | 10/1998 |
| WO | WO 00/06755 A2 | 2/2000 |

OTHER PUBLICATIONS

Patron et al Plant Physiology 2002, 130: 190-198, provided in IDS.*
Edwards et al The Plant Cell 2002, 14: 1767-1785, provided in IDS.*
Salehuzzaman et al 1999, Plant, Cell and Environment 22:1311-1318, provided in IDS.*
Shah N.I.M. Salehuzzaman et al., Expression of a cassava granule-bound starch synthase gene in the amylase-free potato only partially restores amylase content, Plant, Cell, and Environment, vol. 2, pp. 1311-1318, 1999.
Anne Edwards et al., Discrete Forms of Amylose Are Synthesized by Isoforms of GBSSI in Pea, The Plant Cell, vol. 14, pp. 1767-1785, Aug. 2002.
Nicola A. Patron et al., The Altered Pattern of Amylose Accumulation in the Endosperm of Low-Amylose Barley Cultivars Is Attributable to a Single Mutant Allele of Granule-Bound Starch Synthase I with a Deletion in the 5-Non-Coding Region[1], Plant Physiology, vol. 130, pp. 190-198, Sep. 2002.
D.V. Glover et. al., National Quality of Cereal Grains Genetic, vol. 7:183-336, 1987, Corn.
Lloyd W. Rooney et. al., American Association of Cereal Chemists Inc., Chapter 13, pp. 399-429.
J. Jane et. al., Cereal Chemists, vol. 76:629-637, 1999, Effects of Amylopectin Branch Chain Length and Amylose Content on THR Gelatinization and Pasting Properties of Starch.
M.R. Campbell et. al., Cereal Chemistry, vol. 76:552-557, 1999, Prediction of Starch Amylose Content Versus Total Grain Amylose Content in Corn by Near-Infrared Transmittance Spectroscopy.
M. Shure et. al., Cell, vol. 35:225-233, 1983, 1983, Molecular Identification and Isolation of the Waxy Locus in Maize.
Y. Sano et. al., Theor. Appl. Genet., vol. 68:467-473, 1987, Differential Regulation of Waxy Gene Expression in Rice Endosperm.
J.H.M. Hovenkamp et. al., Theor. Appl. Genet., vol. 75:217-221, 1987, Isolation of an Amylose-Free Starch Mutant of the Potato (Solanum Tuberosum L.).
K. Denyer et. al., Plant Cell Environ., vol. 18:1019-1026, 1995, The Isolation and Characterization of Novel Low-Amylose Mutants of Pisum Sativum L.
F.R. Van Der Leij et. al., Theor. Appl. Genet., vol. 82:289-295, 1991, Complementation of the Amylose-Free Starch Mutant of Potato (Solanum Tuberosum.) by the Gene Encoding Granule-Bound Starch Synthase.
A.M. Smith et. al., Annu. Rev. Plant Physiol. Plant Mol. Biol., vol. 48:67-87, 1997, The Synthesis of the Starch Granule.
Isao Hanashiro et. al., Carbohydrate Research, vol. 306:421-426, 1998, Examination of Number-Average Degree of Polymerization and Molar-Based Distribution of Amylose by Fluorescent Labeling With 2-Aminopyridine.

(Continued)

*Primary Examiner*—Anne Marie Grunberg
*Assistant Examiner*—Brent Page

(57) ABSTRACT

The present invention is directed to an isolated starch, a transgenic plant or plant part producing the starch, flour and a thickened foodstuff prepared from a grain capable of producing such isolated starch. The present invention is directed to a method for altering starch amylose composition of a cereal grain.

6 Claims, 8 Drawing Sheets

OTHER PUBLICATIONS

Database WPI, Derwent Publications Ltd., AN 2000-390244, XP-002167085, Kao Corp., Treatment Agent Composition for Textile Product.

Biosciences Information Service, Oct. 1999, Salehuzzaman et. al., Expression of a Cassava Granule-Bound Starch Synthase Gene in the Amylose-Free Potato Only Partially Restores Amylose Content, Database Accession No. PREV1999000527574, XP-002167084 and Plant Cell and Environment vol. 22, No. 10, Oct. 1999, pp. 1311-1318.

S.N.I.M. Salehuzzman et. al., Plant Molecular Biology, vol. 23:947-962, 1993, Isolation and Characterization of a CDNA Encoding Granule-Bound Starch Synthase in Cassava (Manihot Esculenta Crantz) and its Antisense Expression in Potato.

E. Flipse et. al., Theor. Appl. Genet., vol. 88:369-375, 1994, Expression of a Wild-Type GBSS Gene Introduced Into an Amylose-Free Potato Mutant by Agrobacterium Tumefaciens and the Inheritance of the Inserts at the Microsporic Level.

F.R. Van Der Leij et. al., Department of Genetics, p. 177, 1990, Expression of the Gene Encoding Granule Bound Starch Synthase After Introduction in an Amylose-Free and a Wildtype Potato (Solanum Tuberosum).

Roger P. Ellis et. al., Journal of the Science of Food and Agriculture, vol. 77:289-311, 1998, Starch Production and Industrial Use.

Austin H. Young, Starch, Chapter VIIII, pp. 249-276, 1984, Fractionation of Starch, XP-002167083.

Von. R. Ebermann et. al., Starke, vol. 27:329-333, 1975, Bestimmung Der Molekulargewichtsvertilung in Nativen Starken Durch Gelchromatographie.

H. Shimada et. al., Theor. Appl. Genet., vol. 86:665-672, 1993, Antisense Regulation of the Rice Waxy Gene Expression Using a PCR-Amplified Fragment of the Rice Genome Reduces the Amylose Content in Grain Starch.

* cited by examiner

STARCHES PRODUCED BY THE EXPRESSION OF HETEROLOGOUS GRANULE BOUND STARCH SYNTHASE GENES

This application is a Continuation of U.S. patent application Ser. No. 10/362,492 filed on Feb. 21, 2003, now abandoned, which is a National Stage Entry of PCT Application No. PCT/US00/23,494 filed Aug. 28, 2000. The entire contents of each of these applications is incorporated herein by reference.

FIELD OF THE INVENTION

This invention is in the field of plant molecular biology. More specifically, this invention pertains to the modification of amylose content and/or amylose weight distribution in starch by the expression of heterologous granule bound starch synthase polynucleotides.

BACKGROUND OF THE INVENTION

Starch is a mixture of two polysaccharides, amylose and amylopectin. Amylose is an unbranched chain of up to several thousand α-D-glucopyranose units linked by α-(1,4)-glycosidic bonds. Amylopectin is a highly branched molecule made up of up to 50,000 α-D-glucopyranose residues linked by α-(1,4) and α-(1,6) glycosidic bonds. Approximately 5% of the glycosidic linkages in amylopectin are α-(1,6) bonds, which leads to the branched structure of the polymer.

Amylose and amylopectin molecules are organized into starch granules that are stored in plastids. The starch granules produced by most plants are 15 to 30% amylose and 70 to 85% amylopectin. The ratio of amylose to amylopectin and the degree of branching of amylopectin affect the physical and functional properties of the starch. The usefulness and value of starches in food and industrial applications is determined by functional properties such as viscosity and stability. Specific functional properties may be obtained by using the starch from a crop such as corn, rice, potatoes, or wheat which meets said functional properties. If no starch is found which meets the required functional property, such as the need for stable viscosity under high temperatures and acidic conditions, the functionality can usually be achieved by chemically modifying the starch. Various types and degrees of chemical modification are used in the starch industry, and the labeling and use of chemically modified starches must meet government regulations.

Within the starch bearing organs of plants, the proportion of amylose to amylopectin and the degree of branching of amylopectin are under genetic control. For example, corn plants homozygous for the recessive waxy (wx) mutation lack a granule-bound starch synthase enzyme and produce nearly 100% amylopectin. Corn plants homozygous for the recessive amylose extender (ae) mutation and uncharacterized modifier genes can reportedly produce starch granules that are approximately 80 to 90% amylose (see U.S. Pat. No. 5,300,145). The dull mutant of corn lacks a starch synthase distinct from the one lacking in the waxy lines. The starch from the dull mutant is characterized by more amylose and a larger proportion of shorter branches on the amylopectin molecule than normal starch.

Most cereal crops are handled as commodities, and many of the industrial and animal feed requirements for these crops can be met by widely grown and volume-produced common varieties. However, at present, there exists a growing market for crops with special end-use properties not met by grain of standard composition. Most commonly, specialty corn is differentiated from "normal" corn by altered endosperm properties. For example, waxy or high amylose corn contains an overall change in the ratio of amylose to amylopectin, sweet corn contains an increased accumulation of sugars, and food-grade corn and popcorn contain an alteration in the degree of endosperm hardness (Glover, D. V. and Mertz, E. T. (1987) in *Corn: Nutritional Quality of Cereal Grains; Genetic and Agronomic Improvement*, R. A. Olson and K. J. Frey, eds. American Society of Agronomy, Madison Wis., pp. 183-336; Rooney, L. W. and S. O. Serna-Saldivar, (1987) Food Uses of Whole Corn and Dry-milled Fractions, in *Corn: Chemistry and Technology*, S. A. Watson and P. E. Ramstead, eds. American Association of Cereal Chemists, Inc., St. Paul, Minn., pp. 399-429). The present invention offers the buyers of specialty grains a source of starch having properties distinct from starch derived from commodity crops, also known as dent starch, and offers farmers the opportunity to grow a higher value-added crop than conventional or commodity corn.

Purified starch is obtained from plants by a milling process. Starch is extracted from corn kernels through the use of a wet milling process. Wet milling is a multi-step process involving steeping and grinding of the kernels and separation of the starch, protein, oil and fiber fractions. A review of the corn wet milling process is given by S. R. Eckhoff (1992) in the *Proceedings of the Fourth Corn Utilization Conference*, June 24-26, St. Louis, Mo., printed by the National Corn Growers Association, CIBA-GEIGY Seed Division and the United States Department of Agriculture. Wheat is also an important source of purified starch. Wheat starch production is reviewed by J. W. Knight and R. M. Olson (1984) in Starch: *Chemistry and Technology* $2^{nd}$ Edition, Academic Press Whisler et al. Eds.

Starch is used in numerous food and industrial applications and is the major source of carbohydrates in the human diet. Typically, starch is mixed with water and cooked to form a thickened gel. This process is termed gelatinization. Three important properties of a starch are the temperature at which gelatinization occurs, the viscosity the gel reaches, and the stability of the gel viscosity over time. Distinct differences in gelatinization behavior can be found for starches from different crops and for maize starches of different genotypes. These differences may be attributed to variations in the amylose to amylopectin ratio, the composition of the starch and the amylopectin branch-chain distribution. As the temperature of a solution of dent starch in water is increased, viscosity will increase as the starch granules swell and take up water. A maximum viscosity will be attained before the granules rupture and the granule contents are released into solution. With cooling, amylose chains reassociate to form a more organized structure and viscosity will once again increase as a stiff gel is formed. Waxy starches that lack amylose cook at a lower temperature and with cooling tend to form softer gels. However, the amylopectin branch chain distribution of particular waxy starches can also significantly influence gelatinization temperature, viscosity increase and the propensity of a cooked starch to form a stiffened gel (Jane, J. et al (1999) *Cereal Chem.* 76:629-637).

The amylose content in cornstarch affects many physical and functional properties of starch including crystalline structure, pasting temperature, gel formation, and resistance to digestion. In general, as amylose levels are increased, crystallinity as measured by x-ray diffraction or birefringence is decreased, heat capacity and pasting temperature are increased, and stiffer gels are produced (Cheetham, N. W. H. and Leping, T. (1998) *Carbohydr. Polym.* 36:227-228; Kalistratova, E. N. (1999) Starch/Starke 51:160-162; Jane, J. et al. (1999) *Cereal Chem.* 76:629-637). This influence of amylose on starch functional properties is such that, for certain applications, waxy starches, containing no amylose, are preferred. However, the attributes conferred by amylose-containing starches are desirable in certain recognized applications and it is conceivable that additional utility may be further demonstrated. High amylose starches are sources of resistant starch that serve as a dietary fiber. These starches are also of use in food coatings, starch jelly confections, films, and biodegradable plastics (Campbell, M. R. et al. (1999) *Cereal Chem.* 76:552-557).

Synthesis of the two starch polymers and their assembly into the starch granules is an area of intense research. Biosynthesis of amylopectin involves the participation of starch synthases, starch branching enzymes, and starch debranching enzymes via a complex process that, to this day, remains poorly understood. While the roles that these enzymes play in the synthesis of the branched polymer are not completely defined, the critical involvement of a specific starch synthase, granule-bound starch synthase I (GBSSI) in the synthesis of amylose in starch storing tissues has been demonstrated. Mutants lacking this enzyme activity have been identified in corn, potato, rice, and pea (Shure, M. et al. (1983) *Cell* 35:225-233; Hovenkamp-Hermelink, J. H. M. et al. (1987) *Theor. Appl. Genet.* 75:217-221; Sano, Y. (1987) *Theor. Appl. Genet.* 68:467-473; and Denyer, K. et al. (1995) *Plant Cell Environ.* 18:1019-1026). Starch isolated from these mutants contains little, if any, of the linear starch polymer, amylose. Introduction of a wild type potato GBSSI gene into amf potato by *Agrobacterium*-mediated transformation leads to complementation of the genetic defect in this mutant. Granule bound starch synthase activity is restored and amylose levels reach amounts similar to those found in "starch cultivars" of potato (van der Leij, F. R et al. (1991) *Theor. Appl. Genet.* 82:289-295).

Amylose amounts vary with the plant source but generally fall within the range of 15 to 30% of the total starch content. It has been suggested that the amount of amylose that normally accumulates in wild type plants may be determined by one or more factors functioning separately or jointly. These factors may be physical constraints, substrate supply (i.e. ADP-glucose), level of GBSSI activity, or availability of oligosaccharide primers (Smith, A. M. et al. (1997) *Annu. Rev. Plant Mol. Biol.* 48:67-87). Amylose chain length is also found to vary depending upon the botanical source of the starch. An evaluation of amylose samples from 7 different species has indicated that small amylose, with a degree of polymerization (dp) lower than 1000, is predominant in cereals while that with a dp larger than 1000, is found in tuberous plants (Hanashiro, I. and Takeda, Y. (1998) *Carbohydr. Res.* 306:421-426). The degree of polymerization of maize amylose has been reported to be 800 while that of potato is 3000 (Ellis, R. P. et al. (1998) *J. Sci. Food Agric.* 77:289-311). The factors that are responsible for determining amylose level and degree of polymerization in higher plants have not been systematically studied and are not currently known.

In tubers, the ability of a heterologous GBSSI from cassava to complement the amf mutation in potato was recently reported. In this study, *Agrobacterium*-mediated transformation was used to introduce into the amf mutant either a complete copy of the cassava (*Manihot esculentum*) GBSSI coding region, or hybrid versions containing sequences from both the potato and the cassava proteins. One of the hybrid proteins consisted of the potato GBSSI transit peptide fused to the remainder of the mature cassava protein. Another comprised the potato GBSSI transit peptide, the first 89 amino acids of the mature potato GBSSI (containing the substrate-binding site for ADP-glucose) protein followed by the mature cassava GBSSI protein Expression of the native cassava protein gave only partial complementation with amylose levels reaching 8.2% of the total starch. This restores amylose to 37% of the wild type level. Expression of these hybrid proteins gave the best results. The best performing plants accumulated 13% amylose compared to 22% amylose present in the wild type. Only transformants containing the hybrid protein consisting of the transit peptide and the first 89 amino acids of potato GBSSI fused to the remainder of the cassava GBSSI protein accumulated amylose in excess of 10% of the total starch. These levels of amylose polymer were found in only 13% of the transformants expressing this hybrid protein. Physicochemical determinations performed on the transgenic starch confirmed the presence of amylose in the complemented lines. Measured parameters obtained from Bohlin rheometry and differential scanning calorimetry were intermediate between those displayed by wild type and amf starch and were related to the amount of amylose present in the investigated transgenic lines. No measurement of the amylose degree of polymerization was reported. (Salehuzzaman, S. N. I. M. et al. (1999) *Plant Cell Environ.* 22:1311-1318).

Salehuzzaman et al. contend that the failure to completely restore amylose to wild type levels via introduction of a heterologous cassava GBSSI or a potato-cassava hybrid GBSSI protein can be explained by inherent differences in the intrinsic properties of the potato and cassava proteins. Indeed, amylose amounts of 10% or more of the total starch are reached only upon expression of the hybrid protein containing the substrate-binding site for ADP-glucose that is derived from the potato GBSSI protein.

Identification of the factors involved in determining amylose level and degree of polymerization in higher plants will permit the generation of transgenic plants where the levels of amylose and its fine characteristics may be manipulated.

SUMMARY OF THE INVENTION

The present invention is directed to an isolated starch comprising amylose, wherein amylose comprises a number average molecular weight from about $1.5 \times 10^5$ to about $2.4 \times 10^5$ and a weight average molecular weight from about $9.5 \times 10^5$ to about $14.4 \times 10^5$. A transgenic plant or plant part producing the starch is another aspect of the present invention. The transgenic plant may be selected from a cereal crop, such as the group consisting of corn, wheat and rice.

An isolated grain which is capable of producing a starch comprising amylose, wherein amylose comprises a number average molecular weight from about $1.5 \times 10^5$ to about $2.4 \times 10^5$ and a weight average molecular weight from about $9.5 \times 10^5$ to about $14.4 \times 10^5$ is also embodied by the present invention. The present invention is also directed to flour prepared from the isolated grain and a thickened foodstuff prepared with the flour.

Another aspect of the present invention is a starch isolated from a cereal crop, wherein said starch comprises about a fifty percent increase in number average molecular weight relative to commodity starch from the same species of said cereal crop from which said starch was isolated. Yet another aspect of the present invention is an isolated corn starch having a polydispersity of about 4.4 to about 6.3. A further aspect of the present invention is a corn plant capable of expressing in developing seeds a heterologous GBSSI polynucleotide wherein starch produced in grain from the seed comprises amylose of molecular weight greater than amylose of a comodity corn grain.

The present invention is also directed to a method for altering starch amylose composition of a cereal grain comprising generating a construct comprising a full-length GBSSI from species I in sense orientation under the control of a promoter; creating a transgenic plant by inserting said construct into a heterologous plant from species II; growing said transgenic plant under conditions which allow expression of the GBSSI from species I; harvesting grain and isolating starch from said transgenic plant; and comparing starch amylose composition from the transgenic plant with amylose composition of starch isolated from a non-transformed plant of species II. GBSSI may be selected from the group consisting of potato and *Canna edulis*. Species I may be selected from the group consisting of potato and *Canna edulis* and species II may be corn.

The present invention is also directed to a transgenic plant comprising a recombinant DNA sequence comprising a heterologous nucleotide sequence encoding GBSSI under control of a promoter.

BRIEF DESCRIPTION OF THE DRAWINGS AND SEQUENCE LISTINGS

The invention can be more fully understood from the following detailed description and the accompanying drawings and Sequence Listing which form a part of this application.

Figure 8A:
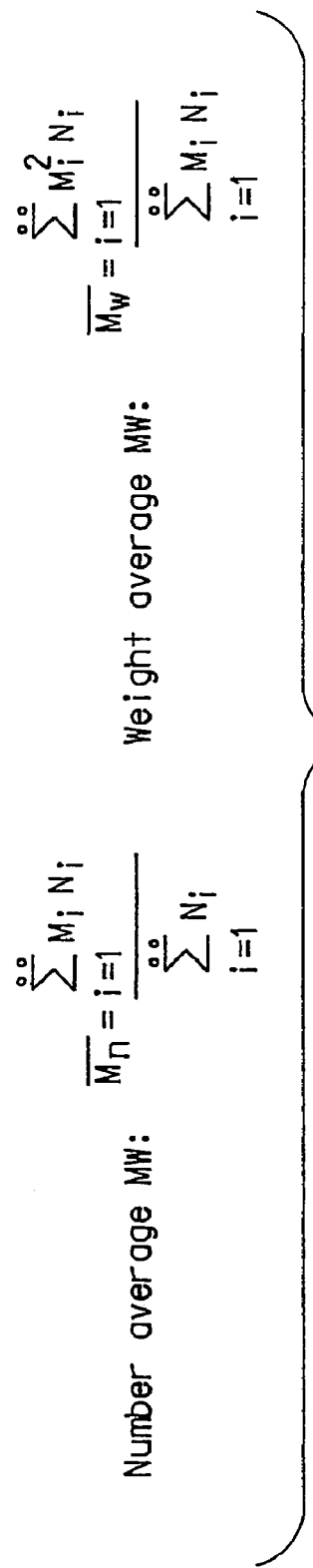
Figure 8B:
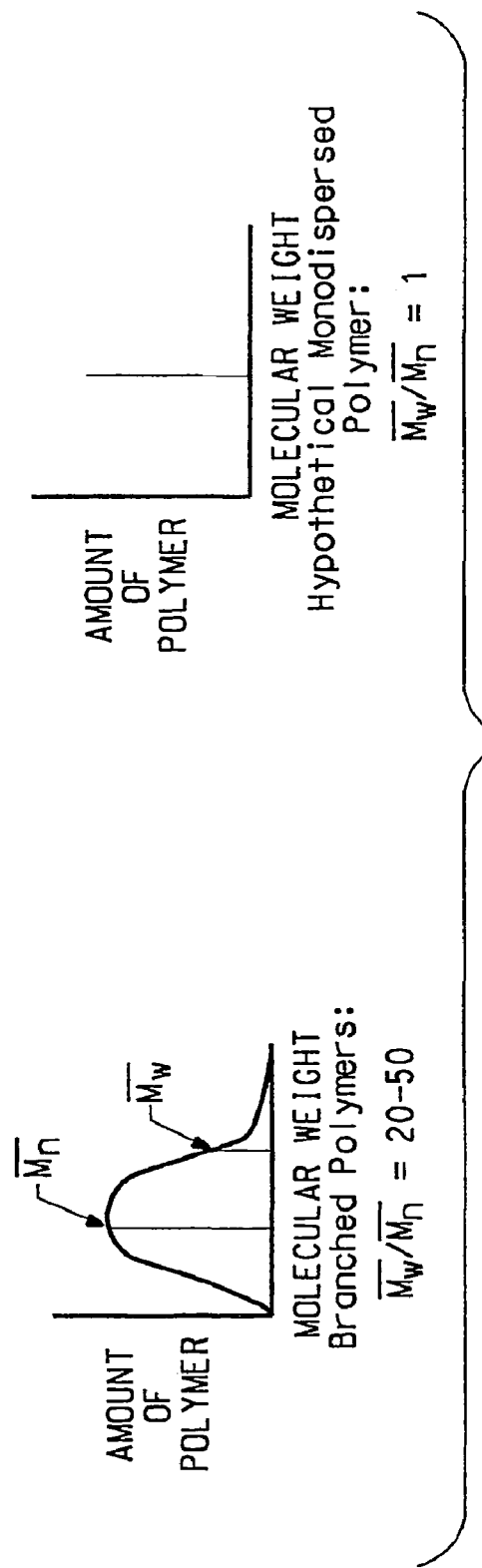

FIG. 8A shows definitions of number average molecular weight and weight average molecular weight. $M_i$ is the mass of the ith polymer chain; $N_i$ is the number of chains with that mass. The width of the molecular weight distribution curve is directly proportional to $\overline{M}w/\overline{M}n$. In addition, FIG. 8B shows graphs depicting number average molecular weight and weight average molecular weight The first graph shows a typical molecular weight distribution. The number average occurs near the peak of the graph; the weight average is shifted down. For typical branched polymers, $\overline{M}w/\overline{M}n$ ranges between 20 and 50. The second graph shows a hypothetical monodisperse polymer (in which all chains have exactly the same mass) for which the number and weight average molecular weights are equal. Thus, for monodisperse polymer, $\overline{M}w/\overline{M}n$ is equal to one (1). Monodisperse polymer distributions do not exist in reality.

The following sequence descriptions and Sequences Listing attached hereto comply with the rules governing nucleotide and/or amino acid sequence disclosures in patent applications as set forth in 37 C.F.R § 1.821-1.825. The Sequence Listing contains the one letter code for nucleotide sequence characters and the three letter codes for amino acids as defined in conformity with the IUPAC-IUB standards described in Nucleic Acids Research 13:3021-3030 (1985) and in the *Biochemical Journal* 219 No. 2):345-373 (1984) which are herein incorporated by reference. The symbols and format used for nucleotide and amino acid sequence data comply with the rules set forth in 37 C.F.R § 1.822.

SEQ ID NO:1 is the nucleotide sequence of the potato GBSSI.

SEQ ID NO:2 is the nucleotide sequence of the oligonucleotide primer ST3 used to amplify the 3' half of the potato GBSSI.

SEQ ID NO:3 is the nucleotide sequence of the oligonucleotide primer ST4 used to amplify the 3' half of the potato GBSSI.

SEQ ID NO:4 is the nucleotide sequence of the oligonucleotide primer KB84 used to amplify the 5' half of the potato GBSSI.

SEQ ID NO:5 is the nucleotide sequence of the oligonucleotide primer ST2 used to amplify the 5' half of the potato GBSSI.

SEQ ID NO:6 is the nucleotide sequence of the entire cDNA insert in clone ect1c.pk007.o15 encoding an entire *Canna edulis* GBSSI.

SEQ ID NO:7 is the nucleotide sequence of the oligonucleotide primer KB102 used to amplify a portion of the *Canna edulis* GBSSI sequence in clone ect1c.pk007.o15 while introducing a Sma I site 8 nt after the termination codon.

SEQ ID NO:8 is the nucleotide sequence of the oligonucleotide primer KB103 used to amplify a portion of the *Canna edulis* GBSSI sequence in clone ect1c.pk007.o15 while introducing a Sma I site 8 nt after the termination codon.

SEQ ID NO:9 is the nucleotide sequence of the oligonucleotide primer KB104 used to amplify a portion of the *Canna edulis* GBSSK sequence in clone ect1c.pk007.o15 while introducing an Nco I site at the methionine start site.

SEQ ID NO:10 is the nucleotide sequence of the oligonucleotide primer KB101 used to amplify a portion of the *Canna edulis* GBSSI sequence in clone ect1c.pk007.o15 while introducing an Nco I site at the methionine start site.

DETAILED DESCRIPTION OF THE INVENTION

In the context of this disclosure, a number of terms shall be utilized.

"Granule-bound starch synthase I" and "GBSSI" is a starch synthase which is exemplified by a nucleotide sequence set forth in SEQ ID NO:1. While it is clear that GBSSI is the protein that synthesizes amylose in storage tissue, the identity and characterization of GBSS enzymes that are responsible for amylose synthesis in tissues that transiently store starch is less well defined. Regardless of the nomenclature, the present invention includes the use of any GBSS that functions primarily in amylose biosynthesis. Various mutants of GBSSI have been shown to contain little, if any, linear starch polymer amylose. For example, corn plants homozygous for the recessive waxy (wx) mutation lack granule-bound starch synthase enzyme and produce nearly all amylopectin.

As used herein, the term "starch" refers to a polysaccharide consisting of α-D-(1,4) glucan that may contain a variable proportion of α-D-(1,6) branches. The isolated starch of the present invention comprises amylose, wherein amylose comprises a number average molecular weight preferably from about $1.5 \times 10^5$ to about $2.5 \times 10^5$, more preferably about $1.6 \times 10^5$ to about $2.4 \times 10^5$, even more preferably about $1.8 \times 10^5$ to about $2.3 \times 10^5$, and having weight average molecular weight preferably from about $9 \times 10^5$ to about $15 \times 10^5$, more preferably from about $9.5 \times 10^5$ to about $14.4 \times 10^5$, more preferably about $9.7 \times 10^5$ to about $12.8 \times 10^5$, and even more preferably about $10 \times 10^5$ to about $12 \times 10^5$. "Number average molecular weight" and "weight average molecular weight" are defined in FIGS. 8A and 8B. Corn starch of the present invention further comprises a polydispersity of about 4.0 to about 5.7, more preferably about 4.4. Furthermore, the starch of the present invention isolated from a cereal crop, comprises preferably about thirty percent, more preferably about forty percent, even more preferably about fifty percent increase in number average molecular weight relative to commodity starch, also known as dent starch, from the same species of cereal crop. The term "isolated starch" refers to a starch that is separated from the environment in which it is found. It may be substantially free from other cellular components such as chromosomal or extrachromosomal nucleic acid sequences. Isolated starch may be purified from a host cell in which it occurs.

A transgenic plant or plant part that produces such starch is also an embodiment of the present invention. As used herein "cereal crops" mean any plant capable of yielding a seed containing starch suitable for food or industrial use. Cereal crops include and are not limited to corn, rice, wheat, barley, oat, rye, as well as sorghum and the like. "Tuberous crops" are those plants producing starchy storage organs including and not limited to potato (such as *Solanum tuberosum*) and *Canna edulis*, formed by swelling of an underground stem or the distal end of a root. The plant part is selected from the following non-limiting group consisting of grain, kernel or seed, root and flower. In addition, products prepared from the plant parts such as and not limited to flour produced from grain, are also embodied by the present invention. Flour produced from the grain, a thickened foodstuff prepared with the flour as well as various industrial applications are other embodiments of the present invention.

The term "starch fine structure" refers to the molecular structure of a starch polymer, the presence, abundance and distribution of $\alpha$-D-(1,6) bonds and the presence, abundance and length of both branched and unbranched $\alpha$-D-(1,4) glucans in the polymer. Starch fine structure is described by amylopectin branch chain distribution, or by the relative proportion of amylose to amylopectin, or by the degree of polymerization of amylose. Alteration of any of these structural molecular components results in an altered starch fine structure. One or more of these parameters may be altered independently of another. The term "degree of polymerization" refers to the number of $\alpha$-D-glucopyranose units in a molecule or designated portion of a molecule such as a branch chain of amylopectin. A preferred embodiment of the present invention comprises a starch with a greater degree of polymerization of amylose. As used herein, the term "branch chain distribution" refers to the distribution of $\alpha$-1,4-linked glucan chains which is detected following isoamylase digestion of amylopectin and subsequent fractionation of the liberated branches by size exclusion chromatography.

The term "pasting" refers to an irreversible physical change in starch granules or a suspension of starch granules characterized by swelling and hydration of granules, a rapid increase in viscosity of a suspension, and the formation of a sol from the suspension. This change is also known as cooking or gelatinization. The abbreviation "SNU" refers to the stirring number unit, approximately equal to 10 centipoise, which is a measure of viscosity. For conversion to SI units (pascal seconds), multiply centipoise by 1000, i.e., 1 PaSec=1000 cp. Hence, 1 SNU=0.01 PaSec. The term "sol" refers to a fluid colloidal system. The term "viscosity" is a measure of the internal friction of a fluid that can be thought of as the consistency or thickness of a fluid.

The terms "polynucleotide", "polynucleotide sequence", "nucleic acid sequence", "sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. The term "isolated polynucleotide" refers to a polynucleotide that is separated from the environment in which it is naturally found. It may be substantially free from other nucleic acid sequences, such as, and not limited to, other chromosomal and extrachromosomal DNA and RNA. Isolated polynucleotides may be purified from a host cell in which they naturally occur. Isolated polynucleotides may be inserted into expression vectors and/or a heterologous host nucleic acid in order to be expressed. These hosts may be prokaryotic, eukaryotic, or viral. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well-established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric or heterologous" "gene or polynucleotide" refers any gene or polynucleotide that is not native to a plant. A chimeric or heterologous gene comprises regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

Accordingly, the present invention is directed to insertion of a polynucleotide of one species into a second species. The present invention encompasses insertion of a heterologous polynucleotide into a commodity cereal. As a result, the commodity cereal may retain the endogenous polynucleotide as well as acquire a foreign polynucleotide for GBSSI.

"Coding sequence" refers to a nucleotide sequence that codes for a specific amino acid sequence. "Initiation codon" and "termination codon" refer to units of three adjacent nucleotides in a coding sequence that specify protein synthesis chain initiation and chain termination, respectively. "Protein synthesis" and "mRNA translation" are interchangeable. "Open reading frame" refers to the amino acid sequence encoded between translation initiation and termination codons of a coding sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements are often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner R. and Foster D. G. (1995) *Mol. Biotechnol.* 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L. W. et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Mature protein" or the term "mature" when used in describing a protein refers to a post-translationally processed polypeptide; i.e., one from which any pre- or propeptides present in-the primary translation product have been removed. "Precursor protein" or the term "precursor" when used in describing a protein refers to the primary product of translation of mRNA; i.e., with pre- and propeptides still present Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Altered levels" or "altered expression" refers to the production of gene product(s) in transgenic organisms in amounts or proportions that differ from that of normal or non-transformed organisms.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Sambrook").

"PCR" or "polymerase chain reaction" is well known by those skilled in the art as a technique used for the amplification of specific DNA segments (U.S. Pat. Nos. 4,683,195 and 4,800,159).

In a preferred embodiment of the present invention, intact heterologous GBSSI sequence from a tuber has been introduced into a way mutant of a cereal. Expression of the heterologous protein, evaluated by iodine staining of corn kernels, is observed in 75% of transformants when a GBSSI sequence from potato is used. Most of the analyzed positive transgenic lines exhibit amylose content greater than or equal to 13% of the total starch. Analysis of the starch indicates that in the transgenic corn plants expressing potato GBSSI, a unique amylose product is synthesized that can be differentiated from that synthesized in commodity crops, such as dent corn, or in potato tubers. Although the present invention encompasses a novel amylose-containing starch, it is not limited to the starches described here. It is expected that the combination of potato GBSSI expression with expression of other transgenes or with other starch mutant genetic backgrounds will lead to the production of further novel amylose-containing starches beyond those demonstrated here.

While not intending to be bound by any theory or theories of operation, Applicants currently believe that the invention includes a change in the starch fine structure derived from a grain of a cereal crop in the relative proportions of amylose to amylopectin relative to that of starch derived from cereal crops not possessing a GBSSI chimeric gene. This invention is believed to involve specific alterations in starch, such as changes in amylose to amylopectin ratio and changes in the degree of polymerization of amylose that can be created by the expression of heterologous GBSSI in transgenic plants.

This invention also concerns a method of preparing a thickened foodstuff comprising combining a foodstuff, water, and an effective amount of a starch isolated from the grain of a cereal crop variety prepared using the method, and cooking the resulting composition as necessary to produce a thickened foodstuff.

This invention also concerns flours prepared from the grain of said cereal crop, and the preparation of foodstuffs such as and not limited to breads, baked goods, pastas, and the like, by combining water, food ingredients, and an effective amount of flour from the grain of cereals crop prepared using the method, and cooking the resulting composition as necessary to produce a foodstuff.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the disclosure. Such modifications are also intended to fall within the scope of the appended claims.

The disclosure of each reference set forth herein is incorporated herein by reference in its entirety.

Example 1

Generation of a Potato Full-Length Sense Granule Bound Starch Synthase I DNA Construct A vector containing the DNA encoding the entire coding region of the potato granule bound starch synthase (GBSSI; SEQ ID NO:1) in sense orientation with respect to the 27 kD Zein promoter and 10 kD zein 3' end was constructed. The coding region was obtained in two segments using a two step RT-PCR strategy. Total RNA was isolated from Russet Burbank potato tubers and was transcribed with reverse transcriptase using an oligo-dT primer. Reverse transcription was carried out using an RT-PCR kit (Perkin-Elmer; Poster City, Calif.) with a 30 minute incubation at 42° C. followed by 5 minutes at 99° C. The reverse transcription product was then used to amplify the 3' half of the potato GBSSI cDNA (nucleotides 776 through 1945) using primers ST3 (SEQ ID NO:2) and ST4 (SEQ ID NO:3) with Vent$_R$®Polymerase (New England Biolabs; Beverly, Mass.) in standard buffer supplied by the manufacturer and following manufacturer's protocols.

```
5'-GTCAATGTACCAGTCCAGAGG-3'              SEQ ID NO:2

5'-GGATCCTCGAGGTTCTACATAGTTCGCTAG-3'     SEQ ID NO:3
```

The PCR product was digested with Eco RI and Xho I, isolated, and ligated into pBluescriptSK+ (Stratagene; La Jolla, Calif.) essentially as described in Sambrook.

The 5' portion of the potato GBSSSI cDNA (nucleotides 47-949) was obtained by amplification of the reverse transcriptase product with an Advantage-GC cDNA kit (Clontech; Palo Alto, Calif.) following the manufacturer's suggested protocol using the oligonucleotide primer pair KB84 (SEQ ID NO:4) and ST2 (SEQ ID NO:5).

```
5'-AAGCTTGATATCCCATGGCAAGCATCACAGCT      SEQ ID NO:4
TC-3'

5'-CAGGCTTCTCATATCCATC-3'                SEQ ID NO:5
```

This resulting PCR product was digested with Eco RV and Eco RI and joined to the 3' fragment already in pBluescriptSK+. The sequence of the fragment containing the complete coding region was determined and compared against the published sequence by generating an artificial potato cDNA sequence via paper splicing of introns and joining of exons defined in Genbank (NCBI general identifier number 21470). Transformants containing DNA fragments whose sequence was identical to that of the published sequence or which contained only silent nucleotide changes that did not alter the encoded amino acid sequence were carried forward. While not intending to be bound by any theory or theories of operation, these silent nucleotide changes are likely to represent polymorphisms due to different genotypes used for isolation of the genomic and cDNA fragments. Compared to the published sequence, SEQ ID NO:1 has 3 nucleotide differences which produce no change in the encoded amino acids and therefore are silent.

Figure 1:
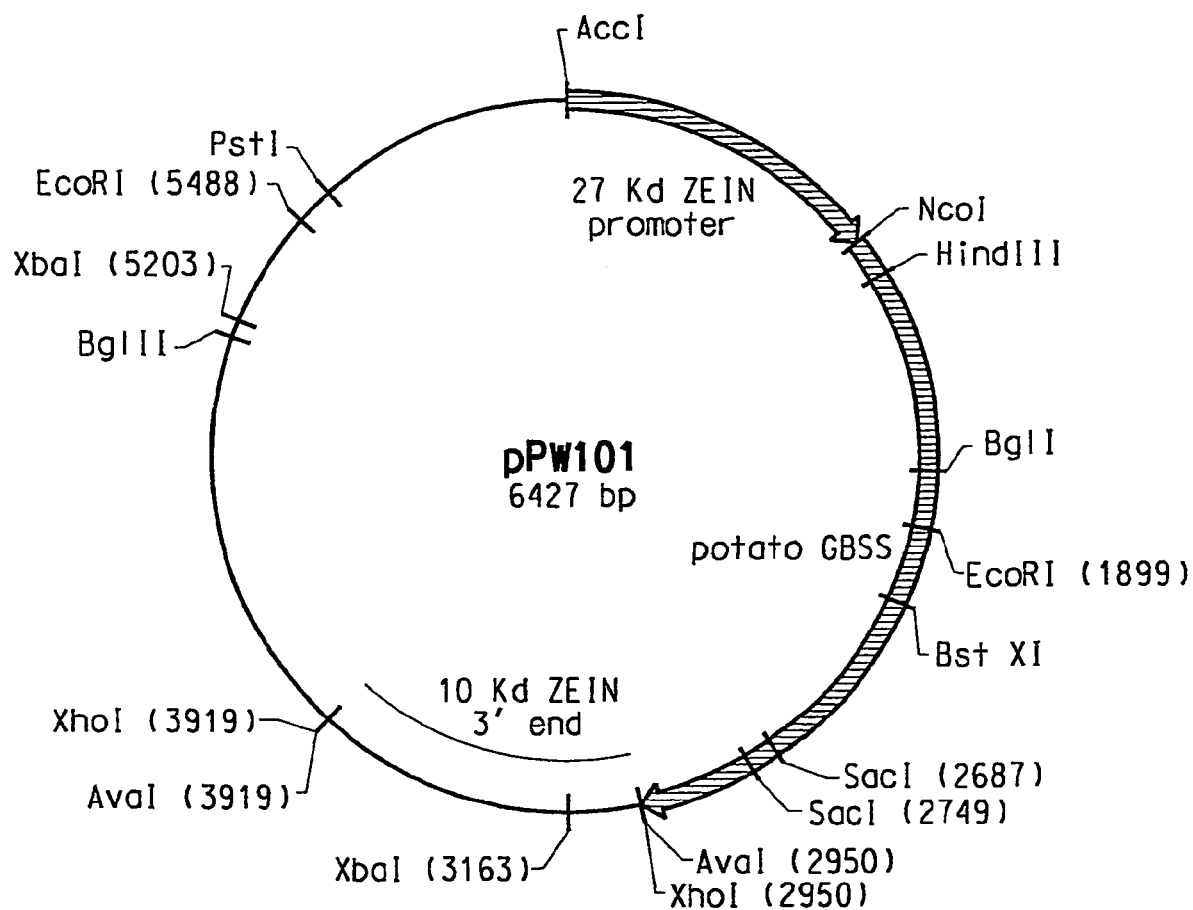
FIG. 1 depicts the plasmid map of pPW101 which contains the entire open reading frame of the potato GBSSI in sense orientation with respect to the maize 27 kD Zein promoter.

One of these transformants, pPW100, containing SEQ ID NO:1, was digested with Xho I, incubated with the Klenow fragment of DNA polymerase to fill-in the S' overhang, and then partially digested with Nco I. The resulting 1905 bp fragment (containing the entire GBSSI open reading frame) was ligated to the 4.53 kb Nco I-Sma I fragment of pSPB38 defined in WO 00/06755, incorporated herein by reference. The Nco I-Sma I fragment from pSPB38 contains a 1.05 Kb Sal I-Nco I promoter fragment of the 27 kD zein gene and a 0.96 kb Sma I-Pvu II fragment from the 3' end of the 100 kD zein gene in the hygromycin resistance vector, pKS17. pKS17 contains the T7 promoter, the hygromycin phosphotransferase (HPT) gene, and the T7 terminator in a chimeric gene on a multicopy vector lacking the β-lactamase gene. The resultant plasmid containing the 27 kD zein-potato GBSSI-10 kD zein 3' end is termed pPW101 and is depicted in FIG. 1.

Example 2

Identification of a *Canna edulis* GBSSI cDNA

A cDNA library was prepared using mRNAs from *Canna edulis* tuber in Uni-ZAP™ XR vector according to the manufacturer's protocol (Stratagene Cloning Systems, La Jolla, Calif.). Conversion of the Uni-ZAP™ XR library into a plasmid library was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al. (1991) *Science* 252:1651-1656). The resulting ESTs were analyzed using a Perkin Elmer Model 377 fluorescent sequencer.

Example 3

Generation of a Full Length Sense *Canna edulis* GBSSI Construct

A vector containing the DNA corresponding to the entire coding region of the *Canna edulis* GBSSI (SEQ ID NO:6) in sense orientation with respect to the 27 kD Zein promoter and 10 kD zein 3' end was constructed. *Canna edulis* ESTs encoding candidate GBSSIs were identified by conducting BLAST (Basic Local Alignment Search Tool; Altschul, S. F., et al., (1993) *J. Mol. Biol.* 215:403-410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 2 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266-272) provided by the NCBI.

The cDNA insert in clone ect1c.pk007.o15 was identified as a candidate GBSSI gene by a BLAST search against the NCBI database due to its homology to granule bound synthases from potato, cassava, and rice. The sequence of the DNA insert of this cDNA clone, pHP16210, is shown in SEQ ID NO:6. A Sma I site was introduced into the sequence 8 nt after the termination codon by performing PCR amplification using the oligonucleotide primer pair KB102 (SEQ ID NO:7) and KB103 (SEQ ID NO:8) with pHP16210 as template DNA using a Perkin-Elmer PCR kit.

```
5'-GACACTGTCAAAGAAGGCTTC-3'              SEQ ID NO:7

5'-AAGAAGGGTACCCGGGGTCATCTCTCATGGAG-3'   SEQ ID NO:8
```

The amplified fragment was digested with Acc I and Kpn I and exchanged with the corresponding region in pHP16210 to give pCW97. An Nco I site was incorporated at the methionine start site of the coding region by PCR using the oligo nucleotide primer pair KB104 (SEQ ID NO:9) and KB101 (SEQ ID NO:10) with pHP16210 as template DNA.

```
5'-GATATCGGATCCATGGCTGCTATGACGGCAT    (SEQ ID NO:9)
C-3'

5'-GTGGAAGAAGCGGACAGTTTC-3'           (SEQ ID NO:10)
```

Figure 2:
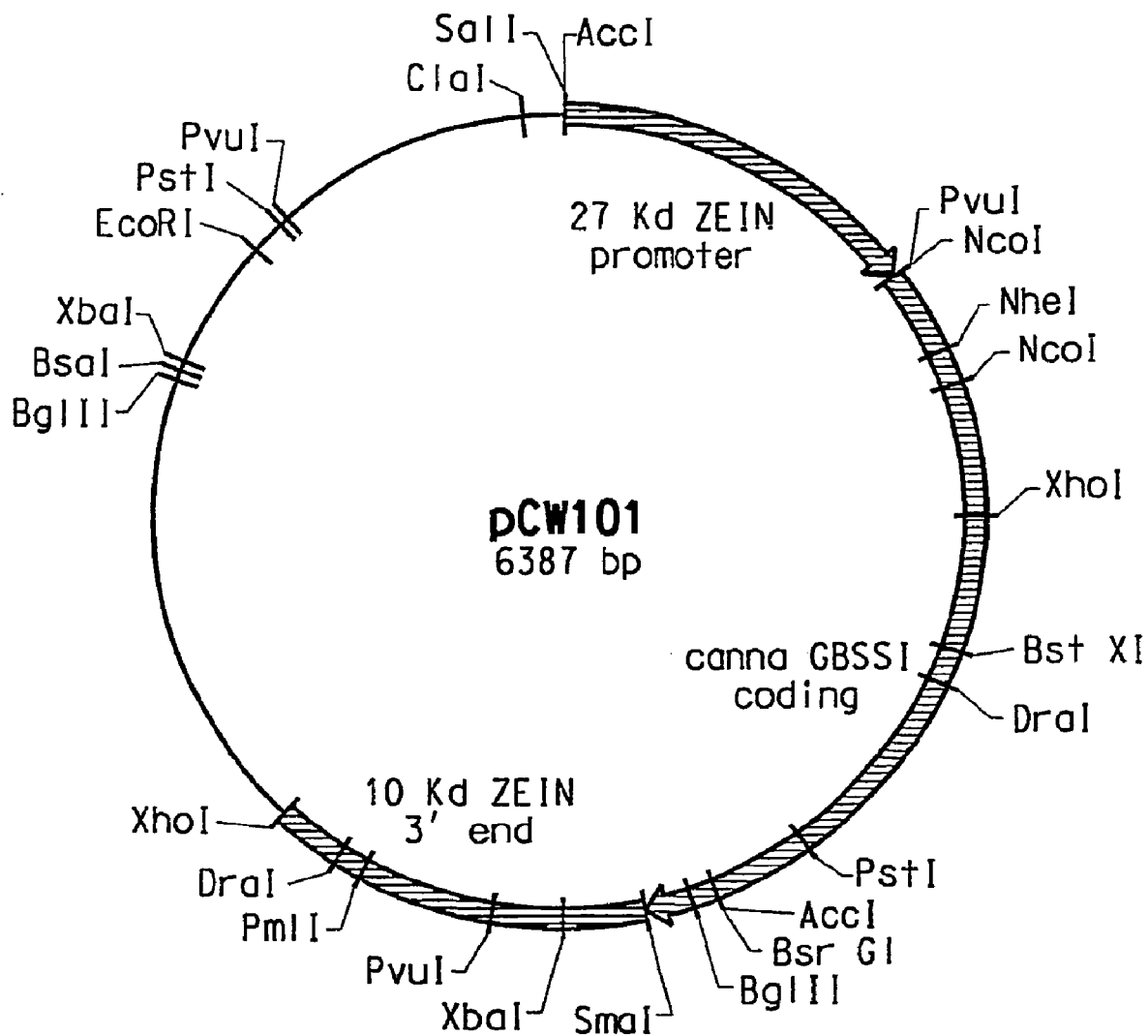
FIG. 2 depicts the plasmid map of pCW101 containing the entire open reading frame of the *Canna edulis* GBSSI in sense orientation with respect to the maize-27 kD Zein promoter.

This PCR fragment was digested with Bam HI and Mfe I and exchanged for the corresponding segment in pHP16210 to give pCW98. This plasmid now contains two Nco I sites, one at the starting methionine and one 312 nucleotides downstream from this point. The modified 3' fragment of pCW97 (containing the added Sma I site) was isolated after digestion with Acc I and Kpn I and inserted into pCW98 that had similarly been cut with these restriction enzymes. The resultant plasmid is termed pCW99. PCW99 was digested with Nco I and Sma I and the resulting 1561 bp fragment was isolated and ligated into the Sma I-Nco I fragment from pSPB38, defined in Example 1, to produce pCW100. The 308 bp Nco I fragment, corresponding to the 5' end of the canna open reading frame, from pCW99 was then added to pCW100. Transformants were screened by restriction enzyme analyses for the presence of and the orientation of the inserted Nco I fragment, leading to the identification of pCW101 which contains 27 kD zein-*Canna* GBSSI-10 kD zein 3' as indicated in FIG. 2.

Example 4

Transformation of Wary Maize with the Potato GBSSI

To determine if the potato sequence was able to complement the waxy mutant, and to analyze the amylose content of the resulting starch, maize waxy callus lines were transformed with the vector containing the potato GBSSI coding region. These callus lines were derived by selfing the F3 plants of a cross between LH195wx and LH132.BC7, which had been selfed and selected both for the waxy phenotype in the endosperm starch and for type II callus production. Immature corn embryos were dissected from developing caryopses 10 to 11 days after pollination when they were 1.0 to 1.5 mm long. The embryos were placed with the axis-side facing down and in contact with agarose-solidified N6 medium (Chu et al. (1975) *Sci. Sin. Peking* 18:659-668). The embryos were kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant was cultured on N6 medium and sub-cultured on this medium every 2 to 3 weeks.

Figure 3:
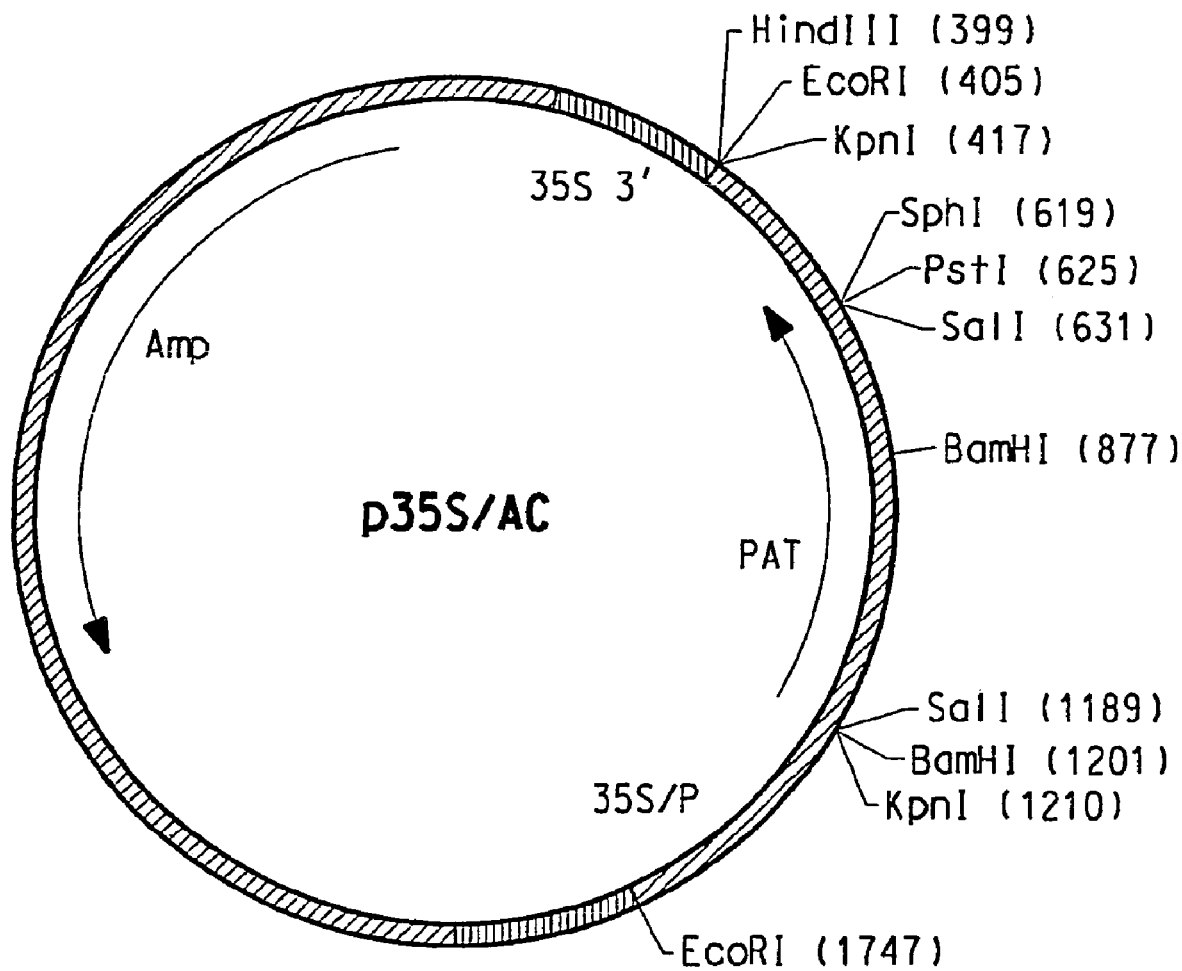
FIG. 3 depicts the plasmid map of p35S/Ac which contains the Pat gene under the control of the 35S promoter from Cauliflower Mosaic Virus.

The plasmid, p35S/Ac (FIG. 3; obtained from Dr. Peter Eckes, Hoechst Ag, Frankfurt, Germany) was used in transformation experiments in order to provide for a selectable marker. This plasmid contains the Pat gene (see European Patent Publication 0 242,236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell, J. T. et al. (1985) *Nature* 313:810-812) and the 3' region of the nopaline synthase gene from the T-DNA of the Ti plasmid of *Agrobacterium tumefaciens*.

The particle bombardment method (Klein, T. et al. (1987), *Nature* 327:70-73) was used to transfer genes to the callus culture cells. Gold particles (1 µm in diameter) were coated with DNA using the following technique. Plasmid DNAs (10 µg of p35S/Ac and 10 µg of pPW101) were added to 50 µl of a suspension of gold particles (60 mg per ml). Calcium chloride (50 µl of a 2.5 M solution) and spermidine free base (20 µl of a 1.0 M solution) were added to the particles. The suspension was vortexed during the addition of these solutions. After 10 minutes, the tubes were briefly centrifuged (5 sec at 15,000 rpm) and the supernatant removed. The particles were resuspended in 200 µl of absolute ethanol, centrifuged again and the supernatant removed. The ethanol rinse was performed again and the particles resuspended in a final volume of 30 µl of ethanol. An aliquot (5 µl) of the DNA-coated gold particles was placed in the center of a Kapton™ flying disc (Bio-Rad; Hercules, Calif.). The particles were accelerated into the corn tissue with a Biolistic™ PDS-1000/He (Bio-Rad Instruments; Hercules, Calif.), using a helium pressure of 1000 psi, a gap distance of 0.5 cm and a flying distance of 1.0 cm.

For bombardment, the embryogenic tissue was placed on filter paper over agarose-solidified N6 medium. The tissue was arranged as a thin lawn and covered a circular area of about 5 cm in diameter. The petri dish containing the tissue was placed in the chamber of the PDS-1000/He approximately 8 cm from the stopping screen. The air in the chamber was then evacuated to a vacuum of 28 inches of Hg. The macrocarrier was accelerated with a helium shock wave using a rapture membrane that bursts when the He pressure in the shock tube reaches 1000 psi.

Seven days after bombardment the tissue was transferred to N6 medium that contained gluphosinate (2 mg per liter) and lacked casein or proline. The tissue continued to grow slowly on this medium. After an additional 2 weeks, the tissue was transferred to fresh N6 medium containing gluphosinate. Six weeks later, areas of actively growing callus measuring about 1 cm in diameter were identified on some of the plates containing the glufosinate-supplemented medium. These calli continued to grow when sub-cultured on the selective medium.

Plants were regenerated from the transgenic callus by first transferring clusters of tissue to N6 medium supplemented with 0.2 mg per liter of 2,4-D. After two weeks the tissue was transferred to regeneration medium (Fromm, M. E. et al. (1990) Bio/Technology 8:833-839). A total of 20 events were produced in a single experiment, S094, carrying the potato GBSSI.

Example 5

Screening of R1 Seeds for Amylose Production

Plants carrying the potato GBSSI construct were either self-pollinated or outcrossed to a homozygous waxy inbred (wxwx) to produce seed for screening. The R1 seeds were initially screened by iodine staining. Lugol's Solution (Iodine/Potassium Iodide Solution, Sigma Chemical L6146) was applied to the starchy endosperm of seeds which had been exposed by crushing single seeds with pliers. A minimum of 6 seeds from each transformation event were screened. Iodine forms a complex with Amylose (Am) that produces a very dark blue-black staining. In contrast, Amylopectin (Ap) does not complex well with iodine and produces a reddish-brown staining. Untransformed waxy (lacking Am), and untransformed dent (wild type and having ~24% Amylose) seeds were used as controls. Occasionally, seed quantity was insufficient to allow destruction of the seeds by crushing. In these cases a portion of the seed crown was removed to expose the starchy endosperm and the seeds were non-destructively stained as above. Fifteen of 20 independent transformation events (75%) carrying the potato GBSSI construct produced some progeny that stained blue/black indicating Am production.

Example 6

Quantitative Analyses of Amylose Content and Molecular Weight from waxy Maize Plants Transformed with the Potato GBSSI Construct Lines identified as Am-producing by the iodine screen were further analyzed to determine the amount of amylose produced and the polymer structure of the amylose. Normal dent corn (24% Amylose) was used for comparison. Starch was extracted from 12 single seeds obtained from each of the Am-producing corn plants transformed with the potato GBSSI construct. Seeds were steeped in a solution containing 1.0% lactic acid and 0.3% sodium metabisulfite, pH 3.82, for 22-24 hours at 52° C. Seeds were drained, rinsed, and homogenized individually in 8-9 mL of a solution of 100 mM NaCl. Five mL of toluene were added to each tube and vigorously shaken twice for 6 minutes using a paint mixer, and allowed to settle for 30 minutes. Two mL of 100 mM NaCl was sprayed onto the solution, allowed to settle for 30 minutes, and the protein-toluene layer was aspirated off. The toluene wash step was repeated. Twelve mL water was added and shaken in a paint shaker for 45 seconds. This solution was centrifuged for 10 minutes and the water was removed. The water wash was repeated, followed by a final wash with 12 mL of acetone. After the shaking and centrifugation steps, the acetone was drained and allowed to evaporate for 1 h. Starch extracts were incubated in a 40° C. oven overnight.

Extracted starches were enzymatically debranched as follows. Extracted starches (7 mg) from individual seeds were gelatinized in 1.1 mL water by heating to 115° C. for 0.5 h. Four units of isoamylase (Sigma) in 50 mM NaOAc buffer, pH 4.5, were added to each of the gelatinized starches and placed in a water bath at 45° C. for 2.5 h. Enzyme inactivation was performed by heating the samples to 115° C. for 5 minutes. The entire reaction was then lyophilized overnight and resuspended in dimethylsulfoxide (DMSO) for gel permeation chromatography (GPC). Ten μL of debranched starch was injected and run through 3 narrow-bore columns (Polymer Labs, Mini-Mix C, D, E with a Mini-mix C guard column) in series at 90° C. and eluted with DMSO at a flow rate of 0.35 mL/min. Sampling interval was 35 minutes. A refractive index detector (Waters, Milford, Mass.) was used with a computer running Waters Millenium32 Chromatography Manager System with GPC option (version 3.05.01) for data collection and analysis. Retention times of pullulan standards (Standard 1: 380K, 100K, 23.7K, 5.8K, 666 and 180 mw, Standard 2: 853K, 186K, 48K, and 12.2K) were used to establish a 3rd order calibration curve and to calculate molecular weight distributions within the Millenium Software. Broad integration parameters (those used to integrate the amylose and amylopectin peaks) were set to: Peak Width=165, Threshhold=20, Minimum Area=200,000, and Minimum Height=2036. Timed events were set to inhibit integration from 0 time through 11.76 minutes (a time before any starch is observed eluting) and from 27.332 minutes (a time after which no starch elutes) until the end of the ran at 35 minutes. Identification of the amylose peak in these debranched starches was accomplished by comparing the elution profiles of debranched starch from waxy maize and normal dent maize to establish the correct time window of amylose elution.

As known to those skilled in the art, different transgenic events produce different levels of the transgene message and consequently can have varying quantitative effects on the property of interest. This is a practical aspect of transgenic plant work, and allows the creation of a range of phenotypes if such a range is desirable. All corn lines that were identified as Am-producing by the above mentioned screen were confirmed as Am-producing by the debranching/GPC analysis. As is also known to those skilled in the art, transgenic corn plants produced by particle bombardment are typically heterozygous for the introduced transgene and will segregate the transgene in a predictable Mendelian fashion. On the selfed ear of an R0 plant, the triploid endosperm, which is the tissue responsible for starch production, will segregate 1:1:1:1 for 0, 1, 2, and 3 copies of the introduced transgene, respectively. On an outcrossed ear of an R0 plant, the transgene will segregate 1:1 for either 0 or 2 copies of the introduced transgene. In the event that the R0 plant was used as a pollinator for a non-transgenic ear, the progeny will segregate 1:1 for either 0 or 1 copy of the transgene. In order to have a reasonable probability of observing any of these transgene dosages, 12 single kernels from each Am-producing line were examined.

Figure 4:
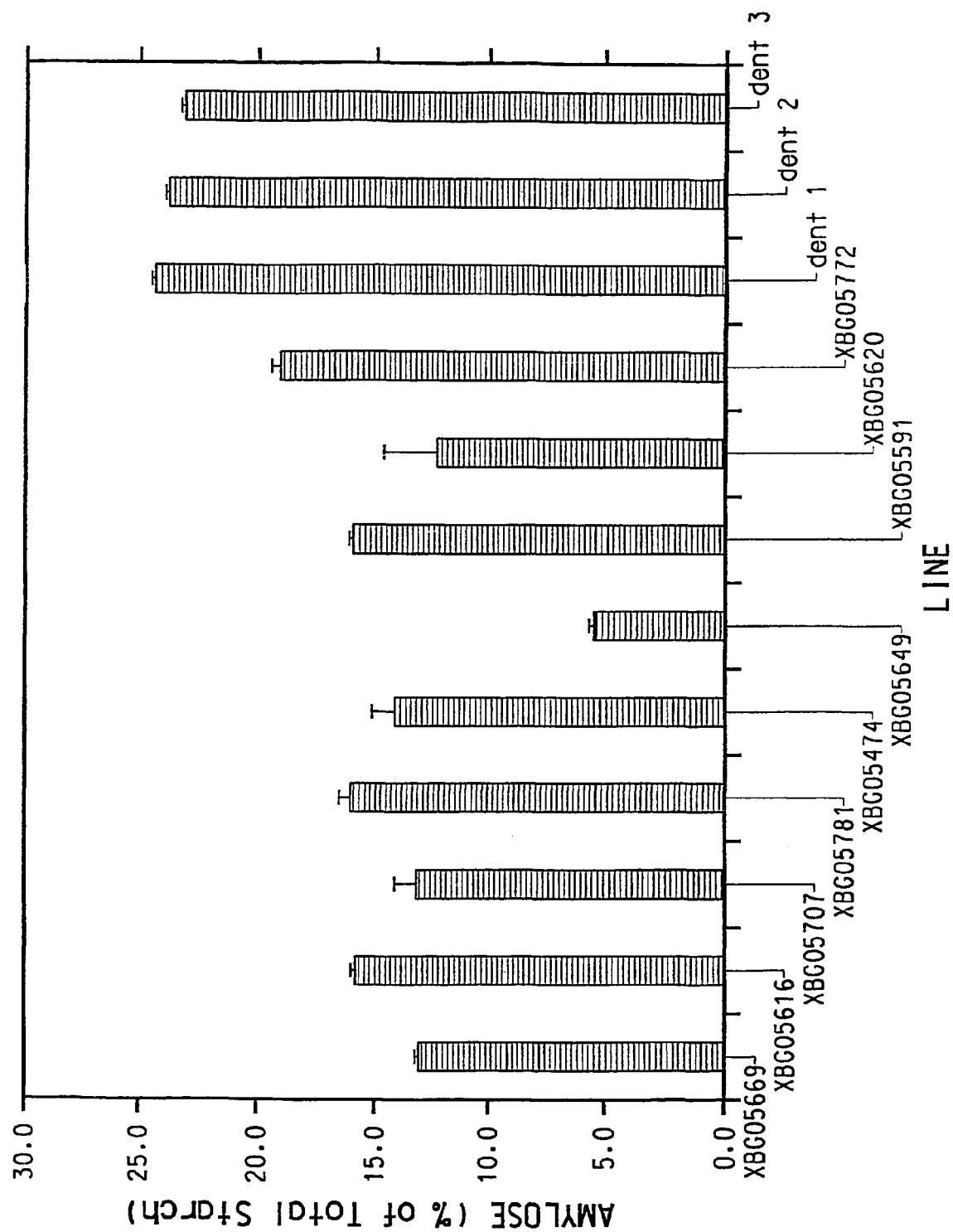
FIG. 4 shows the distribution of the GPC-determined average amylose (Am) content (expressed as a percentage of total starch) of nine Am-producing lines containing the potato GBSSI and three dent controls.

FIG. 4 shows the average amylose content, determined by GPC, for nine Am-producing lines expressing the potato GBSSI and for three dent controls. The Am contents in all Am-producing segregants were averaged for reporting in FIG. 4. It can be seen that a range of Am content is easily created when expressing the potato GBSSI in a waxy maize background. Average Am content ranged from a low 5.8% in line XBG05649 to a high of 19.3% in line XBG05772. Individual seeds in these lines had Am contents as low as 4.1% in XBG05649 to as high as 20.2% in XBG05772. The skilled artisan will recognize that the segregating nature of the introduced gene may, at this stage, account for some of the variation within lines and that such variation can be reduced by standard plant breeding techniques. These results demonstrate a means to produce a range of Am contents between the absence of Am observed in waxy mutants and the normal amount of Am found in dent corn. The skilled artisan will appreciate that this method allows the isolation of any desired amylose content between these two extremes.

Figure 5:
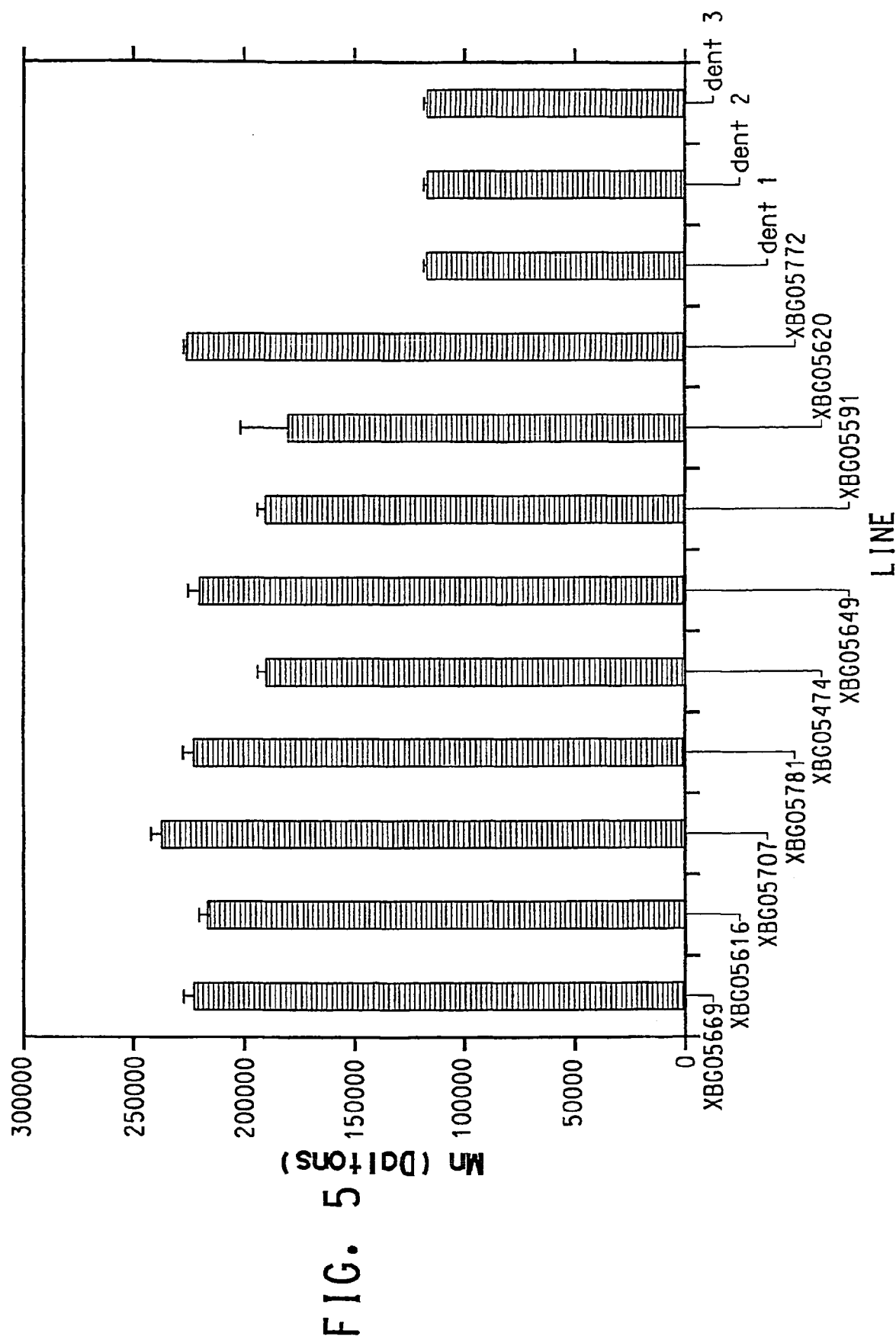
FIG. 5 shows a comparison of the number average molecular weight (Mn) between the Am produced by transformants containing the potato GBSSI and the Am found in normal dent corn
Figure 6:
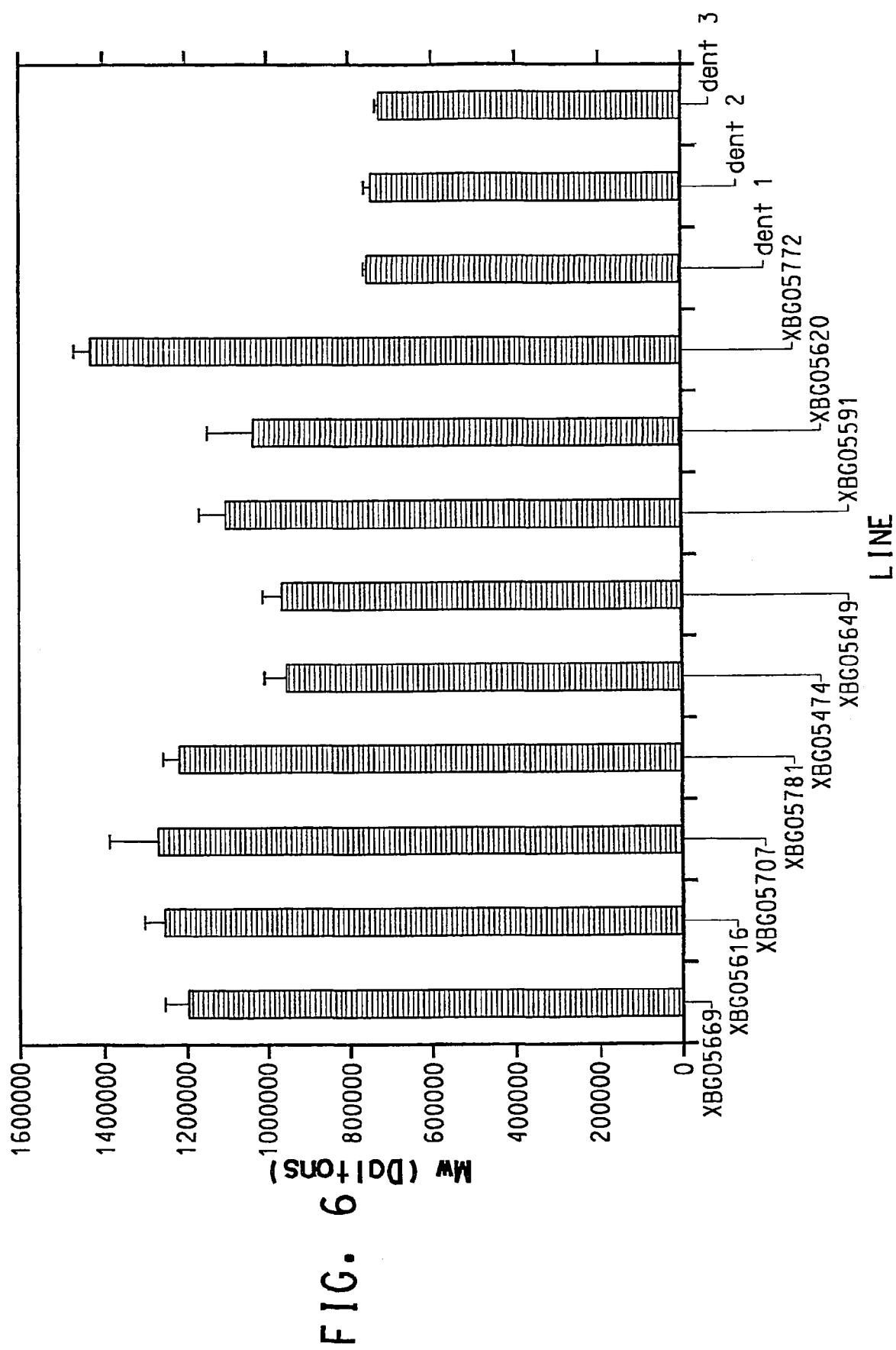
FIG. 6 shows a comparison of the amylose (Am) weight average molecular weight (Mw) distribution (in daltons) found in the Am-producing transformants containing the potato GBSSI and the Am from normal dent corn.
Figure 7:
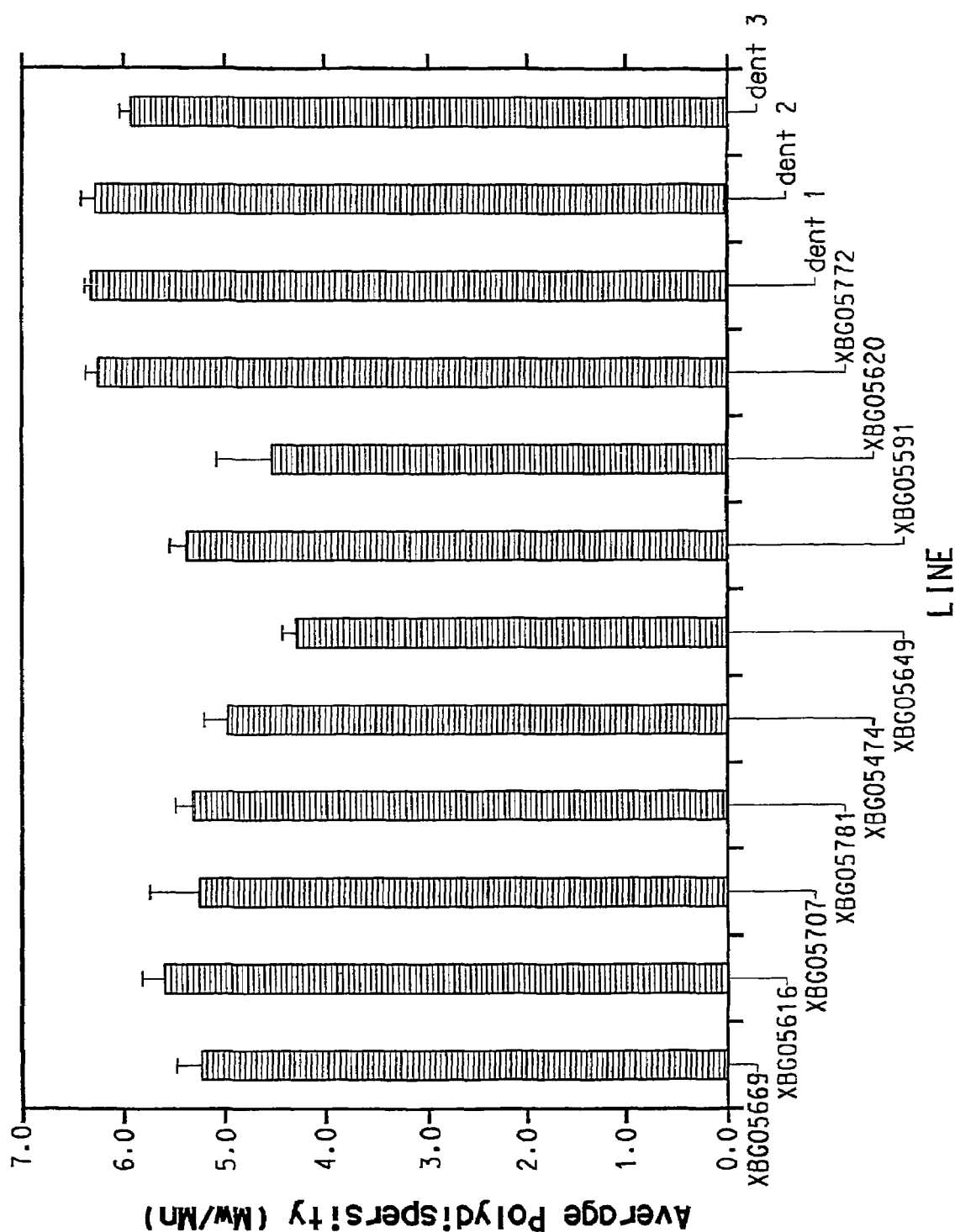
FIG. 7 shows a comparison of polydispersity of normal dent Am and Am from the transformants expressing the potato GBSSI.

Molecular weight distributions of the Am component were compared between normal dent starch and lines containing the potato GBSSI. Molecular weight averages (Mn=number average molecular weight, Mw=weight average molecular weight) and polydispersity (PD=Mw/Mn) were averaged from all the Am-producing seeds within a given line and compared with the average determined for normal dent corn amylose. FIG. 5 shows a comparison of the Mn produced by Am of transformants containing the potato GBSSI and the Am of normal dent corn. Depending on the transformation event, in the Am of transformants containing the potato GBSSI there is a 48% to 95% increase in Mn (number average molecular weight) compared to Am from normal dent corn. FIG. 6 shows a comparison of Mw (weight average molecular weight) between Am produced by transfomants containing the potato GBSSI and Am from normal dent corn. Depending on the transformation event, in transformants containing the potato GBSSI the Mw of Am is increased between 24% and 88% compared to that of normal dent corn. FIG. 7 shows a comparison of polydispersity of normal dent Am and Am from transfomants containing the potato GBSSI. Depending on the transformation event, polydispersity of Am in transformants containing the potato GBSSI ranges from largely unchanged to reduced by as much as 31% when compared to dent corn. Taken together these observations indicate that the Am produced by the potato GBSSI acting in a waxy maize background is inherently different in structure from the Am that normally occurs in dent corn. Weight average molecular weight of Am in maize containing potato GBSSI is higher and is less polydisperse than that of Am normal dent corn. The starch produced in the transgenic maize plants expressing the potato GBSSI is also different than the one produced in potato expressing the same GBSSI gene.

Example 7

Functional Analysis of Starch Produced by Seeds Expressing Potato GBSSI

Individual transgenic lines can be self-pollinated and homozygous individuals identified by standard plant breeding techniques. Once homozygous lines are produced larger samples of starch can be prepared by the following procedure. For each line 15 g of kernels are weighed into a 50 mL Erlenmeyer flask and steeped in 50 mL of steep solution (described in Example 6) for 18 h at 52° C. The kernels are then drained and rinsed with water. The kernels are homogenized using a 20 mm Polytron probe (Kinematica GmbH; Kriens-Luzem, Switzerland) in 50 mL of cold 50 mM NaCl. The homogenate is filtered through a 72 micron mesh screen. The filtrate is brought up to a total volume of 400 mL with 50 mM NaCl and an equal volume of toluene is added. The mixture is then stirred with a magnetic stir bar for 1 h at sufficient speed to completely emulsify the two phases. The emulsion is allowed to separate overnight in a covered beaker. The upper toluene layer is aspirated from the beaker and discarded. The starch slurry remaining in the bottom of the beaker is resuspended, poured into a 250 mL centrifuge bottle and centrifuged 15 minutes at 25,000 RCF. The supernatant is discarded and the starch is washed sequentially with water and acetone by shaking and centrifuging as above. After the acetone wash and centrifugation the acetone is decanted and the starch allowed to dry overnight in a fume hood at room temperature.

A Rapid Visco Analyzer 4 (Newport Scientific; Sydney, Australia) and Thermocline software for Windows (Version 2.0) (Newport Scientific; Sydney, Australia) is used for pasting curve analyses where the starches from potato GBSSI-expressing lines are compared to starch from normal waxy corn. For each line, 1.5±0025 g of starch are put into a new aluminum RVA sample can with 25±1 mL of 0.66% sodium phosphate buffer, pH 6.5. The moisture content of the starch is assumed to be 10%, giving a 5% total solids concentration. The stir lid is placed onto the can and the slurry agitated by spinning the lid. The samples is run under the following profile:

| Paddle Speed: | 0-10 s | 960 RPM |
|---|---|---|
| | 11 s-16 min | 160 RPM |
| Temperature: | 0-1 min. | 50° C. |
| | 1 min.-5 min. | 50° C.→95° C. |
| | 5 min.-8 min. | 95° C. |
| | 8 min.-12 min. | 95° C.→50° C. |
| | 12 min.-16 min. | 50° C. |

Wherein the single temperature indicates holding at that target temperature and the dual temperature listing indicates start and end temperatures over the selected time frame with a constant heating rate increase.

The resulting starch paste can be stored and its retrogradation characteristics observed.

What is claimed is:

1. An isolated starch obtained from maize comprising amylose, wherein said amylose comprises a number average molecular weight from about $1.5 \times 10^5$ to about $2.4 \times 10^5$ and a weight average molecular weight from about $9.51 \times 10^5$ to about $14.41 \times 10^5$, wherein the isolated starch is obtained from seeds, and wherein said maize expresses a potato GBSSI polynucleotide.

2. A transgenic maize plant or plant part transformed with a DNA construct comprising a full length potato GBSSI producing a starch comprising amylose, wherein said amylose comprises a number average molecular weight from about $1.5 \times 10^5$ to about $2.4 \times 10^5$ and a weight average molecular weight from about $9.51 \times 10^5$ to about $14.41 \times 10^5$.

3. An isolated maize grain from a maize plant that expresses a potato GBSSI polynucleotide, wherein said maize grain is capable of producing a starch comprising amylose, wherein said amylose comprises a number average molecular weight from about $1.5 \times 10^5$ to about $2.4 \times 10^5$ and a weight average molecular weight from about $9.51 \times 10^5$ to about $14.41 \times 10^5$.

4. A corn plant that expresses in developing seeds a potato GBSSI polynucleotide wherein starch produced in grain from said seed comprises amylose of molecular weight greater than amylose of a commodity corn grain.

5. A method for altering starch amylose composition of a maize grain comprising:
    a) generating a construct comprising a full-length potato GBSSI in sense orientation under the control of a promoter;
    b) creating a transgenic plant by inserting said construct into a maize-plant;
    c) growing said transgenic plant under conditions which allow expression of the potato GBSSI;
    d) harvesting grain and isolating starch from said transgenic plant; and
    e) comparing molecular weight distributions of the amylose from the transgenic plant with molecular weight distributions of the amylose of starch isolated from a non-transformed maize.

6. A transgenic maize plant comprising a recombinant DNA sequence comprising a heterologous nucleotide sequence encoding a potato GBSSI under control of a promoter.

* * * * *

UNITED STATES PATENT AND TRADEMARK OFFICE
CERTIFICATE OF CORRECTION

PATENT NO. : 7,619,134 B2
APPLICATION NO. : 11/542580
DATED : November 17, 2009
INVENTOR(S) : Broglie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 334 days.

Signed and Sealed this

Twenty-sixth Day of October, 2010

David J. Kappos
*Director of the United States Patent and Trademark Office*

SEQUENCE LISTING

<160> NUMBER OF SEQ ID NOS: 10

<210> SEQ ID NO 1
<211> LENGTH: 2161
<212> TYPE: DNA
<213> ORGANISM: Solanum tuberosum

<400> SEQUENCE: 1

```
cttggtagat tcccttttt gtagaccaca catcacatgg caagcatcac agcttcacac      60
cactttgtgt caagaagcca aacttcacta gacaccaaat caaccttgtc acagatagga     120
ctcaggaacc atactctgac tcacaatggt ttaagggctg ttaacaagct tgatgggctc     180
caatcaagaa ctaatactaa ggtaacaccc aagatggcat ccagaactga gaccaagaga     240
cctggatgct cagctaccat tgtttgtgga aagggaatga acttgatctt tgtgggtact     300
gaggttggtc cttggagcaa aactggtgga ctaggtgatg ttcttggtgg actaccacca     360
gcccttgcag cccgcggaca tcgggtaatg acaatatccc cccgttatga ccaatacaaa     420
gatgcttggg atactagcgt tgcggttgag gtcaaagttg gagacagcat tgaaattgtt     480
cgtttctttc actgctataa acgtgggtt gatcgtgttt ttgttgacca cccaatgttc     540
ttggagaaag tttggggcaa aactggttca aaaatctatg gccccaaagc tggactagat     600
tatctggaca atgaacttag gttcagcttg ttgtgtcaag cagccctaga ggcacctaaa     660
```

-continued

```
gttttgaatt tgaacagtag caactacttc tcaggaccat atggagagga tgttctcttc    720
attgccaatg attggcacac agctctcatt ccttgctact tgaagtcaat gtaccagtcc    780
agaggaatct atttgaatgc caaggtcgct ttctgcatcc ataacattgc ctaccaaggc    840
cgattttctt tctctgactt ccctcttctc aatcttcctg atgaattcag gggttctttt    900
gatttcattg atggatatga gaagcctgtt aagggtagga aaatcaactg gatgaaggct    960
gggatattag aatcacatag ggtggttaca gtgagcccat actatgccca agaacttgtc   1020
tctgctgttg acaagggtgt tgaattggac agtgtccttc gtaagacttg cataactggg   1080
attgtgaatg gcatggatac acaagagtgg aacccagcga ctgacaaata cacagatgtc   1140
aaatacgata taaccactgt catggacgca aaacctttac taaaggaggc tcttcaagca   1200
gcagttggct tgcctgttga caagaagatc cctttgattg gcttcatcgg cagacttgag   1260
gagcagaaag gttcagatat tcttgttgct gcaattcaca agttcatcgg attggatgtt   1320
caaattgtag tccttggaac tggcaaaaag gagtttgagc aggagattga acagctcgaa   1380
gtgttgtacc ctaacaaagc taaggagtg gcaaaattca atgtcccttt ggctcacatg   1440
atcactgctg gtgctgattt tatgttggtt ccaagcagat ttgaaccttg tggtctcatt   1500
cagttacatg ctatgcgata tggaacagtg ccaatctgtg catcgactgg tggacttgtt   1560
gacactgtga agaaggcta tactggattc catatgggag ccttcaatgt tgaatgcgat   1620
gttgttgacc cagctgatgt gcttaagata gtaacaacag ttgctagagc tcttgcagtc   1680
tatggcaccc tcgcatttgc tgagatgata aaaaattgca tgtcagagga actctcctgg   1740
aaggaacctg ccaagaaatg ggagacattg ctattgggct taggagcttc tggcagtgaa   1800
cccggtgttg aagggaaga aatcgctcca cttgccaagg aaaatgtagc cactccctaa   1860
atgagctttg gttatccttg tttcaacaat aagatcatta agcaaacgta tttactagcg   1920
aactatgtag aaccctatta tggggtctca atcatctaca aaatgattgg tttttgctgg   1980
ggagcagcag catattaggc tgtaaaatcc tggttaatga ttttgtaggt aagggctatt   2040
taaggttgtg tggatcaaag tcaatagaaa atagttatta ctaacgtttg caactaaata   2100
cttagtaatg tagcataaat aatactagta gctaatatat atgcgtgaat ttgttgtacc   2160
t                                                                   2161
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 2

```
gtcaatgtac cagtccagag g                                              21
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 3

```
ggatcctcga ggttctacat agttcgctag                                     30
```

<210> SEQ ID NO 4
<211> LENGTH: 34

```
<212> TYPE: DNA
<213> ORGANISM: Artificial Sequence
<220> FEATURE:
<223> OTHER INFORMATION: Description of Artificial Sequence:PCR primer

<400> SEQUENCE: 4
aagcttgata tcccatggca agcatcacag cttc                                34

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:PCR primer

<400> SEQUENCE: 5
caggcttctc atatccatc                                                 19

<210> SEQ ID NO 6
<211> LENGTH: 2183
<212> TYPE: DNA
<213> ORGANISM: Canna edulis

<400> SEQUENCE: 6
gcacgaggga agctcctcac ttgtcgctgc gagcaagagc aagtccttca atctgagtga      60
gagtggtgaa tgacgtgagc atattccaat ggctgctatg acggcatcac acttcatctc     120
aaatagttca tgctccatct tcaatggagc ttttgattct gtggtgacgt ctttccaaag     180
cagaaggatt ccattctcca gcaaccacac taataattat gaagggctga gaactcggaa     240
tgtggtggat tcacgtaaaa cgcggatgac tgcgaaggca acttctaggc tagctaggag     300
ggttactcga catgccagcc aaagaccctt gattgttgct gtctgtggaa ctggaatgaa     360
cttggggttt gttggttgtg aggtagctcc atggagcaaa actgggggcc ttggcgatgt     420
tcttatagga ttgccacctg ctatggctgc aattgggcac agggtcatga ccgtggcgcc     480
acgatatgac caatataaag atatctggga tacaagtgtc ccagttgagt taaaagttgg     540
ggataagatt gaaactgtcc gcttcttcca ctgctacaaa aggggagttg atcgggtttt     600
tgtggatcac cctatgtttc tcgagaaggt ttggggaaa acaggaggaa aattatatgg     660
tcctgttaca ggaacagatt atgcagacaa tcaactaaga ttcagccttt tgtgcctggc     720
agctctggaa gctccaagac ttctaaatct caacaacagc aaatactatt ctggaccata     780
tggagatgat gttgtgttta ttgccaacga ttggcattct gctctactgc cctgctactt     840
gaaaactatg taccaatcac atggtattta catgaatgct aaggttgcat tttgcattca     900
taatattgct taccagggcc gatttgcctt ttcggacttt gaactcctta atctccccaa     960
taaatttaaa tcttcatttg atttcatgga tggatatgac aaacctgtga aggaaggaa    1020 aataaattgg atgaaggctg gaataataga atgtgatagg tgcttgaccg tgagcccata    1080
ttatgcccaa gagcttgtct caggggtaga aagggtgtt gagttgggca atatcctgcg    1140
catgaaaacc atctgtggaa tagtaaatgg gatggacacc acggagtgga atccattaac    1200
agacaaatat atttctacaa actacgatgc aacaactgta ttggatgcaa aacctctctg    1260
taaggaagct ttgcaagctg agtgtgggct gcctgttaac aaaaacaagc ttgttttggc    1320
ctttgttgga agactagatg agcagaaagg ctcagacatt ctagctgcag caattccaga    1380
acttctttgt gagaatgttc aagtgatagt acttggcact ggcaagaaga agttggagag    1440
tgaacttaca ttacttgagg aaatgttccc agacaaattc agagcacatc tcaaattcaa    1500
```

-continued

```
cgttcctttta gctcatgcaa tcatggcagg agctgatatc cttgttattc caagcagatt      1560
cgaaccctgt ggcctcattc agcttcaggc catgcgatat ggaactctcc ctatgtgtag      1620
caccactggt ggacttgttg acactgtcaa agaaggcttc actggcttcc atatgggccc      1680
cttcagtgtg gagtgtgatg ccgtagacaa agctgatgta caaaagattg tcgaaaccac      1740
gaaaagggcc ctcaaagtct atggaacacc tgcttttgtg gagatgatca agaactgcat      1800
gaaccaagat ctctcatgga agggacctgc aaagaagtgg gaacaatttc tcctgagcat      1860
gggggctgct ggcagtgaac ctggaattga tggggaggaa atagctcctc ttgccaagga      1920
aaatgtagct actccatgag actgaataat actttcctct ttagtcatag tcctaagcct      1980
tgttgtaaag ataaataatc atcctccaaa acctccatcg acatgatgta tccttcacga      2040
gcttggataa attccaagag tttttatata agcagttatg tagtcgtcaa tctgtatgga      2100
aaatccatca atgaaatttt tttattgatg gctattaatc ttaggccagt atttgatgtt      2160
tgtgtaaaaa aaaaaaaaaa aaa                                              2183
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 7

```
gacactgtca aagaaggctt c                                                 21
```

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:PCR primer

<400> SEQUENCE: 8

```
aagaagggta cccgggggtca tctctcatgg ag                                    32
```

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:PCR primer

<400> SEQUENCE: 9

```
gatatcggat ccatggctgc tatgacggca tc                                     32
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 10

```
gtggaagaag cggacagttt c                                                 21
```